United States Patent [19]

Iizuka et al.

[11] Patent Number: 4,853,463

[45] Date of Patent: Aug. 1, 1989

[54] AMINO ACID DERIVATIVES

[75] Inventors: Kinji Iizuka; Tetsuhide Kamijo; Tetsuhiro Kubota, all of Nagano; Kenji Akahane, Tokyo; Hideaki Umeyama, Chiba; Yoshiaki Kiso, Osaka, all of Japan

[73] Assignee: Kissei Pharmaceutical Co., Ltd., Japan

[21] Appl. No.: 283,694

[22] Filed: Dec. 13, 1988

Related U.S. Application Data

[63] Continuation of Ser. No. 903,803, Sep. 4, 1986, abandoned.

[30] Foreign Application Priority Data

Sep. 4, 1985 [JP] Japan .................................. 60-195563

[51] Int. Cl.$^4$ .................. C07C 103/50; C07D 233/64; C07D 413/12
[52] U.S. Cl. ..................................... 530/323; 544/106; 544/159; 544/176; 548/336; 560/126; 560/129
[58] Field of Search ................ 530/323; 544/106, 159, 544/176; 548/326; 560/126, 129

[56] References Cited

U.S. PATENT DOCUMENTS

| | | | |
|---|---|---|---|
| 4,234,571 | 11/1980 | Nestor et al. | 514/15 |
| 4,548,926 | 10/1985 | Matsueda et al. | 514/19 |
| 4,591,648 | 5/1986 | Jones et al. | 548/344 |
| 4,595,677 | 6/1986 | Riniker et al. | 514/17 |
| 4,656,269 | 4/1987 | Iizuka et al. | 548/336 |
| 4,666,888 | 5/1987 | Raddatz et al. | 514/18 |
| 4,668,770 | 5/1987 | Boger et al. | 530/331 |
| 4,698,329 | 5/1987 | Matsueda et al. | 514/18 |
| 4,711,958 | 12/1987 | Iizuka et al. | 544/139 |

FOREIGN PATENT DOCUMENTS

| | | |
|---|---|---|
| 77028 | 4/1983 | European Pat. Off. . |
| 77029 | 4/1983 | European Pat. Off. . |
| 81783 | 6/1983 | European Pat. Off. . |
| 114993 | 8/1984 | European Pat. Off. . |
| 173481 | 3/1986 | European Pat. Off. . |
| 0200406 | 12/1986 | European Pat. Off. . |
| 871004248 | 7/1988 | European Pat. Off. . |
| 39149 | 8/1983 | Japan . |
| 103230 | 12/1984 | Japan . |
| 19100 | 8/1985 | Japan . |
| 201036 | 4/1986 | Japan . |
| 273913 | 7/1986 | Japan . |
| 13908 | 12/1986 | Japan . |
| 265921 | 12/1986 | Japan . |
| 267947 | 12/1986 | Japan . |
| 285317 | 12/1986 | Japan . |
| 268415 | 6/1987 | Japan . |

OTHER PUBLICATIONS

Iizuka et al, Chemical Abstracts, vol. 106, 1987, 106:96160h, "Renin-Inhibiting Histidine Derivatives as Antihypertensives".
Kokubo et al., "Highly Potent and Specific Inhibitors of Human Renin," Biochemical and Biophysical Research Communications, vol. 118, pp. 929-933, 1984.
106th Annual Meeting of Pharmaceutical Society of Japan (Apr. 1986)-Iizuka et al. presentation.
The 50th Annual Meeting of the Japanese Circulation Society (Mar. 1986)-Aoi et al., Abstract followed by presentation.
50th Annual Meeting of the Japanese Circulation Society (Mar. 1986) Miyazaki et al. abstr.
59th General Meeting of the Japanese Pharmacological Society (Apr. 1986) Miyazaki et al. abstr. & presentation.
Brown et al., "Protection of Histidine Side-Chains, etc.", Chemical Abstracts 95:220299f (1981).
Colombo et al., "Acid-Labile Histidine Side-Chain Protection," Chemical Abstracts 101:23914n (1984).
Matsueda et al, "Short Chain Peptide Inhibitors of Human Renin", Chemistry Letters, Chem. Soc. Japan, No. 7, pp. 1041-1044 (1985).
Patent Abstracts of Japan, unexamined applications, C Section, vol. 2, No. 43, Mar. 23, 1978, p. 4928, Applications 51-66243, 51-66244, and 51-67001.

*Primary Examiner*—Morton Foelak
*Assistant Examiner*—Nathan M. Nutter
*Attorney, Agent, or Firm*—Sughrue, Mion, Zinn, Macpeak & Seas

[57] ABSTRACT

Novel amino acid derivatives useful as a therapeutic agent are disclosed. These amino acid derivatives and the pharmaceutically acceptable salts thereof have a human renin inhibitory effect when administered orally and are useful for treatment of hypertension, especially renin-associated hypertension.

15 Claims, No Drawings

AMINO ACID DERIVATIVES

This is a continuation of application Ser. No. 06/903,803, filed 9/4/86, now abandoned.

FIELD OF THE INVENTION

This invention relates to novel amino acid derivatives useful as a therapeutic agent. More particularly, this invention relates to amino acid derivatives which have a human renin inhibitory effect when administered orally, and thus which are useful for treatment of hypertension, especially reninassociated hypertension.

BACKGROUND OF THE INVENTION

Renin is a proteolytic enzyme having a molecular weight of about 40,000, produced and secreted by juxtaglomerular cells in the kidney. This acts on the plasma renin substrate, angiotensinogen, to yield decapeptide angiotensin I which is converted into angiotensin II by an angiotensin I converting enzyme.

It is well known that angiotensin II contracts the vascular smooth muscle and acts on the adrenal cortex to secrete the aldosterone which regulates salts and water balance. Accordingly, the reninangiotensin system plays an important role in hypertension. In fact, a specific inhibitor of angiotensin I converting enzyme has been investigated and developed as a practical medicament for hypertension. Thus, an effective inhibitor of renin has long been sought as an agent for treatment of hypertension, especially renin-associated hypertension. As a result, it has been found that certain peptides show a renin inhibitory effect, as described in Japanese Patent Applications (OPI) Nos. 155345/84, 227851/84 and 110661/84, (The term "OPI" as used herein refers to an unexamined Japanese patent application); Japanese Patent Publication No. 39149/83, Biochemical and Biophysical Research Communications, Vol. 118, pages 929–933, 1984; and European Patent Application Nos. 77029(A$_2$), 77028(A$_2$) and 81783(A$_2$).

Of these prior art references, Japanese Patent Application (OPI) No.155345/84 discloses peptides represented by the following formula:

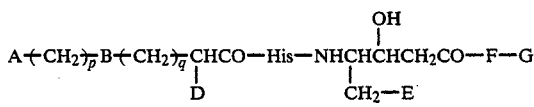

wherein A represents a hydrogen atom, a phenyl group or 10,11-dihydro-5H-dibenzo[a,d]cycloheptenyl group, B represents —O—, —CH=CH— or —CH$_2$—, p and q may be the same or different and each represents an integer of from 0 to 3, D represents a hydrogen atom, a lower alkyl group, a lower alkenyl group, a phenyl group or a phenylalkyl group, E represents a phenyl group, a cyclohexyl group or an isopropyl group, His represents an L-histidyl group, F represents a residual group of an amino acid such as an L-leucyl, an L-isoleucyl, an L-leucyl-L-phenylalanayl, an L-phenylalanyl-L-phenylalanyl and an L-alanyl-L-phenylalanyl group, and G represents a protective group attached to the terminal carbon atom of an amino acid, such as an amino group, an alkylamino group, an arylalkylamino group and an alkoxy group.

Japanese Patent Application (OPI) No. 227851/84 also discloses peptides represented by the following formula:

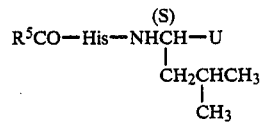

wherein R$^5$CO— represents an aliphatic acyl group, an aromatic acyl group, an aromatic aliphatic acyl group, a heterocyclic acyl group or a heterocyclic aliphatic acyl group, said acyl groups may be substituted with an amino, a protected amino, a hydroxy, a substituted dithio, an alkyl, an alkoxy, an alkoxycarbonyl, or a nitro group or a halogen atom; U represents a formyl group, or

wherein R$^6$ represents a hydrogen atom, an alkyl group, an alkyl group having a hydroxy, a mercapto, an amino, a carbamoyl, a formayl an aromatic ring or a heterocyclic ring substituent; Z represents a hydroxy, a mercapto or a formyl group, or U represents

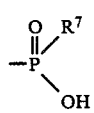

wherein R$^7$ represents a hydroxy group or an alkyl group having a hydroxy, a mercapto, an amino, a carbamoyl, or a formyl group, or an aromatic ring or a heterocyclic ring substituent; His represents an L-histidyl group; C represents a carbon atom in the S-configuration, provided that, when U represents a formyl group, R$^5$CO— does not represent a benzyloxycarbonyl-L-phenylalanyl group or a benzyloxycarbonylL-prolyl-L-phenylalanyl group.

The noted Biochemical and Biophysical Research Communications article discloses a peptide represented by the formula:

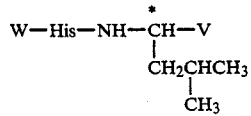

wherein W represents a benzyloxycarbonyl group, an N-benzyloxycarbonyl-L-phenylalanyl group or an N-Benzyloxycarbonyl-3-(1naphthyl)-L-alanyl group, V represents a formyl group or a hydroxymethyl group and C represents a carbon atom in the L-configuration.

Japanese Patent Publication No. 39149/83 discloses peptides represented by the following formula:

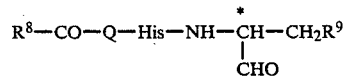

wherein R$^8$ represents a methyl group, an ethyl group, a benzyl group, an adamantyl group or a benzyloxy group, Q represents an L-phenylalanyl group, an L-prolyl-L-phenylalanyl group or an L-histidyl-L-prolyl-L-phenylalanyl group, His represents an L-histidyl group, $R^9$ represents an isopropyl group, and C represents a carbon atom in the L-configuration. These peptides show a renin inhibitory effect however, they are easily hydrolyzed by proteolytic enzymes of the gastorointestinal tract such as chymotrypsins. Therefore, these peptides have drawback that their renin inhibitory effect can not be expected with they are administered orally.

On the other hand, the peptides disclosed in the above European Patent Applications are polypeptides and have difficulties in their preparation and purification. Furthermore, they lose their pharmacological effects when administered orally similar to the peptides disclosed in the Japanese Patent Publication No. 39149/83, and their utility is thus limited.

Furthermore, the following peptide compounds were reported to have a human renin inhibitory activity in 106th Annual Meeting of the Pharmaceutical Society of Japan. (April, 1986) and The Meeting of Japanese Circulation Journal (March, 1986), respectively:

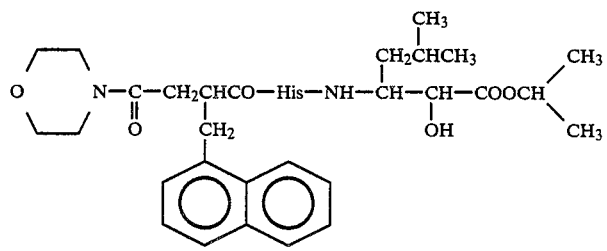

wherein His represents an L-histidyl group.

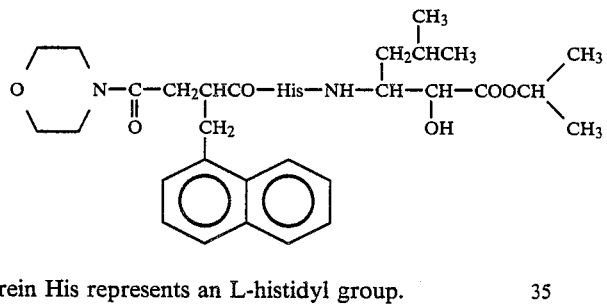

wherein His represents an L-histidyl group.

Thus, development of renin inhibitors which can display a sufficient therapeutic effect by oral administration has long been desired.

SUMMARY OF THE INVENTION

Accordingly, an object of this invention is to provide new amino acid derivatives which exhibit a specific renin inhibitory effect when administered orally to mammalia including humans.

Another object of this invention is to provide new amino acid deriviatives and pharmaceutically acceptable salts thereof.

A further object of this invention is to provide pharmaceutical compositions comprising dipeptides or pharmaceutically acceptable salts thereof.

A still further object of this invention is to provide methods for the treatment of hypertension using new amino acid derivatives or pharmaceutically acceptable salts thereof.

Other objects, features and advantages of this invention will be apparent from the following description of the invention.

The present invention provides new amino acid derivatives represented by formula (I):

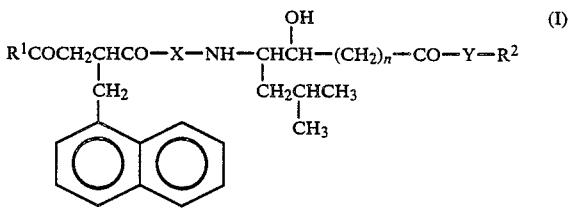

wherein $R^1$ represents

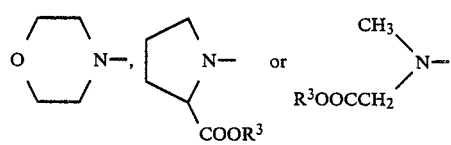

in which $R^3$ represents a lower alkyl group, X represents an amino acid residual group selected from glycine, alanine, B-alanine, valine, leucine, phenylalanine, tryptophane and serine, n is zero or 1, Y represents —O—, or —NH—, and $R^2$ represents a straight- or branched-chain alkyl group having 1 to 7 carbon atoms, and a pharmaceutically acceptable acid addition salt thereof.

DETAILED DESCRIPTION OF THE INVENTION

These amino acid derivatives of formula (I) of the present invention and pharmaceutically acceptable salts thereof inhibit a renin activity in a human renin-sheep renin substrate system. Furthermore, the amino acid derivatives of the present invention are stable against proteolytic enzymes such as pepsin and chymotrypsin.

These findings demonstrate that the amino acid derivatives of formula (I) of the present invention exhibit a human renin inhibitory effect when administered orally to mammalia, including humans, and thus are sueful for treatment of hypertension, especially renin-associated hypertension.

The amino acid derivatives of formula (I) of the present invention can be prepared according to well known method. That is, the amino acid derivatives of the present invention represented by formula (I):

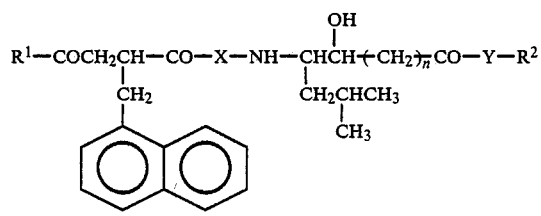

wherein $R^1$, X, n, Y and $R^2$ have the same meanings as defined above; can be prepared by condensing a compound represented by formula (II):

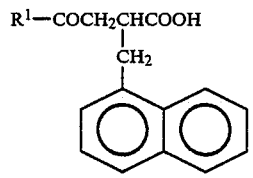

wherein $R^1$ has the same meaning as defined above; with a compound represented by formula (III):

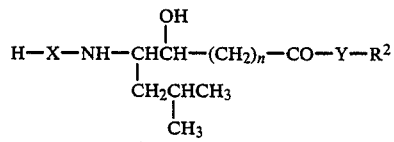

wherein X, n, Y and $R^2$ have the same meanings as defined above; with diphenylphosphoryl azide.

The compounds of formula (II) used as starting materials can be prepared by a method described in literature or an analogous method thereof. For example, the acid compounds represented by formula (II) can be prepared by reacting 1-naphthaldehyde with diethyl succinate to obtain the compound represented by formula (IV):

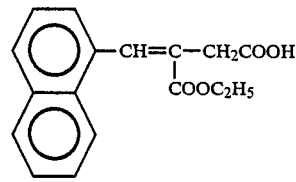

hydrolyzing the resulting compound to obtain the corresponding dicarboxylic acid, dehydrating the dicarboxylic acid compound in acetic anhydride to obtain an succinic anhydride compound represented by formula (V):

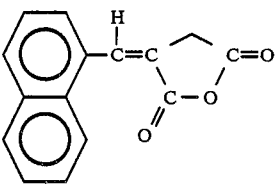

reacting the succinic anhydride compound with an amine represented by formula (VI):

wherein $R^1$ has the same meaning as defined above; to obtain a compound represented by formula (VIII):

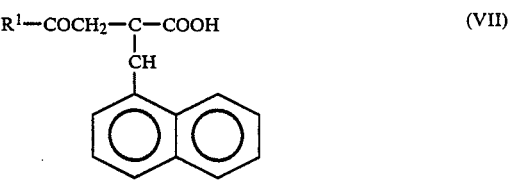

wherein $R^1$ has the same meaning as defined above; and then hydrogenating the resulting compound over palladium charcoal.

The compounds represented by formula (III) used as starting materials can be prepared by condensing an N-protected amino acid and a compound represented by the formula (VIII):

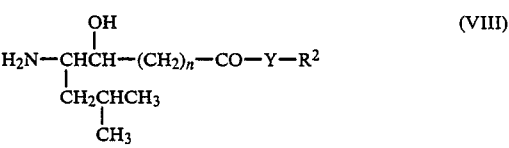

wherein n, Y and $R^2$ have the same meanings as defined above; with diphenylphosphoryl azide, and then removing the protective group from the amino group.

The compound of formula (VIII) can be prepared by a method described in literature or an analogous method thereof. That is, the compound wherein n is 0 can be prepared by esterifing or amidating 3-amino-2-hydroxy-5-methylhexanoic acid which is prepared according to the method described in J. Org. Chem., Vol. 45, pages 2288–2290, 1980. The compound wherein n is 1 can be prepared by esterifing or amidating statine or N-(tert-butyloxycarbonyl)statine.

The reaction of a compound represented by formula (II) with a compound of formula (III) can be carried out according to the following manner.

That is, the amino acid derivative of formula (I) of the present invention can be prepared by dissolving compounds of formulae (II) and (III) in an equimolar amount in N,N-dimethylformamide, adding successively diphenylphosphoryl azide and triethylamine to the solution with stirring under ice-cooling, and stirring the mixture overnight, and then treating the reaction mixture according to usual manner.

The amino acid derivative of formula (I) of the present invention can also be prepared by condensing a compound represented by formula (IX):

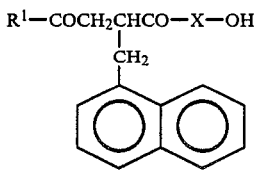

$$R^1-COCH_2CHCO-X-OH \quad (IX)$$
$$| \atop CH_2$$

wherein $R^1$ and $X$ have the same meanings as defied above; and a compound represented by formula (VIII) with diphenylphosphoryl azide.

The compounds of formula (IX) used as starting materials can be prepared by condensing a carboxylic acid compound of formula (II) and an amino acid ester compound with diphenylphosphoryl azide, and then hydrolyzing the resulting compound.

The reaction of a compound represented by formula (IX) and a compound represented by formula (VIII) can be preferably carried out by dissolving a compound of formula (IX) and a compound of formula (VIII) in an equimolar amount to the compound of formula (IX) in N,N-dimethylformamide, adding successively diphenylphosphoryl azide and triethylamine to the solution with stirring under ice-cooling, and stirring the mixture overnight, and then treating the reaction mixture according to usual manner.

The amino acid derivatives represented by formula (I) of the present invention can be converted according to conventional methods to a pharmaceutically acceptable salt thereof. Examples of such pharmaceutically acceptable salts include pharmaceutically acceptable inorganic or organic acid salts such as a hydrochloric acid salt, a sulfuric acid salt, a p-toluenesulfonic acid salt, an acetic acid salt, a citric acid salt, a tartaric acid salt, a succinic acid salt, a fumaric acid salt and the like. These salts have a renin inhibitory effect as high as the corresponding compound having a free amino group, and are stable against proteolytic enzymes, and thus they show the desired renin inhibitory effect even by oral administration.

The amino acid derivatives represented by formula (I) of the present invention possess a strong inhibitory effect on human renin, for example, the amino acid derivatives of formula (I) produce a 50% inhibition in a human renin-sheep renin substrate system and in a human high renin plasma at $3.9 \times 10^{-7}$ to $6.6 \times 10^{-9}$ and $5.1 \times 10^{-7}$ to $3.3 \times 10^{-9}$ molar concentrations, respectively, and reduce blood pressure of marmoset in a high renin state with a low toxicity, and thus are useful as a therapeutically active agent for treatment of hypertension, especially renin-associated hypertension.

The amino acid derivatives represented by formula (I) and the pharmaceutically acceptable salts thereof of this invention have three to five asymmetric carbons and thus there are several steric isomers. In this invention, those isomers or a mixture thereof can be employed.

The amino acid derivatives represented by formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The amino acid derivatives and the pharmaceutically acceptable salt of the formula (I) of the present invention can be administered in various dosage forms depending upon the intended therapy. Typical dosage forms which can be used are tablets, pills, powders, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanaol, and disintegrants such as laminaria and agar. The tablets if desired, can be coated into sugar-coated tablets, gelatin-coated tablets, film-coated tablets, or tablets coated with two or more layers.

When the pharmaceutical composition is formulated into an injectable preparation, it is preferred that the resulting injectable solution and suspension are sterilized and rendered isotonic with respect to blood. In making the pharmaceutical composiotn in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the amino acid derivatives of the present invention may be in a range of from about 5 mg to 5,000 mg per adult human by oral administration per day, or from about 1 mg to 1,000 mg per adult human by parenteral administration per day in multiple doses depending upon the type of disease, the severity of condition to be treated, and the like.

This invention is further illustrated in more detail by way of the following examples and reference examples. The melting point of the product obtained was uncorrected. The NMR spectra of the products were measured by JEOL's High Resolution NMR Spectrometer Type JNM-GX 270. The Mass spectra of the products were measured by JEOL's Mass Spectrometer Type JMS-DX 300 according to the FAB method. Thin layer chromatography was carried out using Merck's pre-coated plates silica gel 60 $F_{254}$ and column chromatography was carried out by employing Merck's Kiesel gel 60 (230–400mesh). Thin layer chromatography was carried out by using a lower layer of a mixture of chloroform, methanol and water in proportion of 8/3/1 (by volume) (mixture A) and a mixture of chloroform and methanol in proportion of 5/1 (by volume) (mixture B) as developing solvents, and an $Rf_1$ (mixture A) value and $Rf_2$ (mixture B) value were calculated.

REFERENCE EXAMPLE 1

2-(1-Naphthylmethyl)-3-(morpholinocarbonyl)-propionic acid

To a solution of 32.3 g of ethyl succinate and 29.0 g of 1-naphthaldehyde in 320 ml of an absolute ethyl alcohol was added 10.7 g of a 50% sodium hydride (dispersion in mineral oil) under ice-cooling, and the mixture was heated under reflux for 30 minutes. To the reaction mixture was added 230 ml of a 1N-aqueous sodium hydroxide solution, and the mixture was concentrated under reduced pressure. To the residue was added water, and the mixture was extracted with ethyl ether to remove neutral materials. The aqueous layer was acidified with a concentrated hydrochloric acid, and extracted with ethyl ether. The ethereal layer was washed with a saturated sodium chloride aqueous solution, dried over anhydrous magnesium sulfate and evaporated under reduced pressure. To the residue was added benzene, and precipitated crystals were collected by filtration to obtain 26.5 g of 2-(1-naphthylmethylene) succinic acid as yellow crystals.

A mixture of 24.5 g of the 2-(1-naphthylmethylene)-succinic acid obtained and 260 ml of acetic anhydride was heated for 60 minutes at 60° C. The reaction mixture was evaporated under reduced pressure, and to the residue was added a mixture of benzene and hexane (1:1). Precipitated crystals were collected by filtration to obtain 16.0 g of 2-(1-naphthylmethylene)succinic anhydride as orange yellow crystals.

A solution of 1.00 g of 2-(1-naphthylmethylene)succinic anhydride and 0.37 g of morpholine in 31 ml of dry dichloromethane was stirred for 2 hours. The reaction mixture was evaporated under reduced pressure, and the residue was crystallized from a mixture of ethyl acetate, benzene and hexane (1:1:1) to obtain 1.10 g of 2-(1-naphthylmethylene)-3-(morpholinocarbonyl)propionic acid as colorless crystals.

A solution of 1.00 g of the propionic acid compound in 40 ml of methyl alcohol was hydrogenated over 0.1 g of a 10% palladium charcoal under a hydrogen atmosphere. After filtration of the catalyst, the filtrate was evaporated under reduced pressure. The residue was crystallized from hexane to obtain 0.90 g of 2-(1-naphthylmethyl)-3-(morpholinocarbonyl)propionic acid as a white powder.

$Rf_1$: 0.67
MS: MH+, 328
Melting point: 64–68° C.
IR (KBr): $\nu$co 1720, 1640 cm−
NMR (CDCl$_3$)
δ: 2.35–2.7(m, 2H), 3.05–3.85(m, 11H), 7.25–8.2(m, 7H)

REFERENCE EXAMPLE 2

The following acid compounds were prepared in an analogous manner described in Reference Example 1.

2-(1-Naphthylmethyl)-3-(2S-methoxycarbonylpyrrolidinocarbonyl)propionic acid

White powder
$Rf_1$: 0.65
IR (KBr): $\nu$co 1740, 1640 cm−

N-{4-(1-Naphthylmethyl)-3-carboxy}butylylglycine methyl ester

White powder
$Rf_1$: 0.68
IR (KBr): $\nu$c 1740,1640 cm−1

REFERENCE EXAMPLE 3

Isopropyl (2RS, 3S)-3-amino-2-hydroxy-5-methylhexanoate hydrochloride

Hydrogen chloride was passed into a solution of 4.0 g of (2RS, 3S)-3-amino-2-hydroxy-5methylhexanoic acid in 50 ml of isopropyl alcohol with stirring under ice-cooling. To the reaction solution was added 100ml of benzene, and the mixture was heated under reflux for 10 minutes with removal of water as formed during the reaction using a molecular seives. The reaction mixture was evaporated under reduced pressure to obtain 5.7 g of isopropyl (2RS, 3S)-3-amino-2-hydroxy-5-methylhexanoate hydrochloride as a white powder.

IR (KBr): $\nu$co 1725 cm−1
NMR (D$_2$O)
δ: 0.8–1.1(m, 6H), 1.29(d, 6H, J=6.6Hz), 1.5–2.0(m, 3H), 3.6–3.75(m, 1H), 4.3–4.7(m, 1H), 5.0–5.2(m, 1H)

REFERENCE EXAMPLE 4

The following ester compound was prepared in an analogous manner described in Reference Example 3.

Methyl (2RS, 3S)-3-amino-2-hydroxy-5-methylhexanoate hydrochloride

White powder
IR (KBr): $\nu$co 1740 cm−1
NMR (D$_2$O)
δ: 0.85–1.0(m, 6H), 1.4–1.9(m, 3H), 3.65–4.7(m, 1H)

REFERENCE EXAMPLE 5

Statylisoamylamide hydrochloride

To a solution of 100 mg of N-(tert-butyloxycarbonyl)statine (commercially available) and 42 mg of isoamylamine in a mixture of 3ml of tetrahydrofuran and 3 ml of N,N-dimethylformamide were added successively 79 mg of 1-hydroxybenzotriazol and 83 mg of dicyclohexylcarbodiimide with stirring under ice-cooling, and the mixture was stirred for 16 hours under ice-cooling. After filtration of precipitates, the filtrate was evaporated under reduced pressure and to the residue was added ethyl acetate. The mixture was chilled, and precipitates were filtered off. The ethyl acetate layer was washed successively with a 5% aqueous sodium bicarbonate solution and a saturated sodium chloride aqueous solution, dried over anhydrous magnesium sulfate, and evaporated under reduced pressure. The residue was purified with silica gel flash column chromatography (eluent: chloroform/methanol=40/1 by volume) to obtain 125 mg of N-(tert-butyloxycarbonyl)-statyl isoamylamide as a colorless viscous oil. [IR (neat): $\nu$co 1685, 1640 cm−1].

To a solution of the amide compound in 5 ml of methanol was added 3.6 ml of a 2N-hydrochloric acid, and the mixture was heated for 1 hour at 60° C. The reaction mixture was evaporated under reduced pressure to obtain 112 mg of statylisoamylamide hydrochloride as a colorless viscous oil. [IR (neat): $\nu$co 1640 cm−1].

REFERENCE EXAMPLE 6

Isopropyl (2RS, 3S)-3-(L-alanyl)amino-2-hydroxy-5-methylhexanoate hydrochloride.

To a solution of 61 mg of N-benzyloxycarbonyl-L-alanine and 79 mg of isopropyl (2RS, 3S)-3-amino-2-hydroxy-5-methylhexanoate hydrochloride in 5 ml of N,N-dimethylformamide were added successively 0.071 ml of diphenylphosphoryl azide and 0.125 ml of triethylamine with stirring under ice-cooling, and the mixture was stirred overnight. The reaction mixture was evaporated under reduced pressure, and to the residue was added a 5% aqueous sodium bicarbonate solution. The mixture was extracted with ethyl acetate and the ethyl acetate layer was washed with water, dried over anhydrous magnesium sulfate and evaporated under reduced pressure. The residue was purified with silica gel flash column chromatography (eluent: chloroform/methanol=20/1 by volume) to obtain 56 mg of isopropyl (2RS, 3S)-3-(N-benzyloxycarbonyl-L-alanyl)amino-2-hydroxy-5-methylhexanoate as a colorless viscous oil.

To a solution of 56 mg of the isopropyl hexanoate compound in 3ml of methanol were added 0.2 ml of a 2N-hydrochloric acid and 20 mg of a 10% of palladium charcoal, and the mixture was hydrogenated under a hydrogen atmosphere. After filtration of the catalyst, the filtrate was evaporated under reduced pressure to obtain 42 mg of isopropyl (2RS, 3S)-3-(L-alanyl)amino-2-hydroxy-5-methylhexanoate hydrochloride as a colorless viscous oil.

$Rf_1$: 0.46
IR (neat): $\nu co$ 1720, 1670 $cm^{-1}$

REFERENCE EXAMPLE 7

The following amino acid derivatives were prepared in an analogous manner described in Reference Example 6.

Isopropyl (2RS, 3S)-3-(L-leucyl)amino-2-hydroxy-5-methylhexanoate hydrochloride

White powder
$Rf_1$: 0.29
IR (KBr): $\nu co$ 1720, 1660 $cm^{-1}$

Isopropyl (2RS, 3S)-3-(L-valyl)amino-2-hydroxy-5-methylhexanoate hydrochloride

White powder
$Rf_1$: 0.61
IR (KBr): $\nu co$ 1720, 1640 $cm^{-1}$

Isopropyl (2RS, 3S)-3-(L-phenylalanyl)amino-2-hydroxy-5-methylhexanoate p-toluenesulfonic acid salt White powder
$Rf_1$: 0.33
IR (KBr): $\nu co$ 1720, 1670 $cm^{-1}$ Isopropyl (2RS, 3S)-3-(L-tryptophyl)amino-2-hydroxy-5-methylhexanoate hydrochloride White powder $Rf_1$: 0.05
IR (KBr): $\nu co$ 1720, 1670 $cm^{-1}$ Isopropyl (2RS, 3S)-3-(L-seryl)amino-2-hydroxy-5-methylhexanoate hydrochloride White powder
$Rf_1$: 0.43
IR (KBr): $\nu co$ 1715, 1670 $cm^{-1}$ Isopropyl (2RS, 3S)-3-glycylamino-2-hydroxy-5-methylhexanoate p-toluenesulfonic acid salt White powder
$Rf_1$: 0.27
IR (KBr): $\nu co$ 1720, 1680 $cm^{-1}$ Isopropyl (2RS, 3S)-3-($\beta$-Alanyl)amino-2-hydroxy-5-methylhexanoate hydrochloride Colorless viscous oil
$Rf_1$: 0.31
IR (neat): $\nu co$ 1730, 1650 $cm^{-1}$

REFERENCE EXAMPLE 8

2-(1-Naphthylmethyl)-3-morpholinocarbonylpropionyl-L-leucine

To a solution of 300 mg of 2-(1-naphthylmethyl)-3-morpholinocarbonyl propionic acid and 183 mg of L-leucine methyl ester hydrochloride in 5 ml of N,N-dimethylformamide were added 0.20 ml of diphenylphosphoryl azide and 0.28 ml of triethylamine with stirring under ice-cooling, and the mixture was stirred overnight. The reaction mixture was evaporated under reduced pressure, and to the residue was added a 5% aqueous sodium bicarbonate solution. The mixture was extracted with ethyl acetate, and the ethyl acetate layer was washed with water, dried over anhydrous magnesium sulfate and evaporated under reduced pressure to obtain 390 mg of 2-(1-naphthylmethyl)-3-morpholinocarbonylpropionyl-L-leucine methyl ester as a white powder.

To a solution of 380 mg of the ester compound in 5 ml of methyl alcohol was added 0.92 ml of a 1N aqueous sodium hydroxide solution with stirring under ice-cooling, and the mixture was stirred overnight. The reaction mixture was evaporated under reduced pressure, and water was added to the residue. The mixture was washed with ethyl ether. The aqueous layer was adjusted to a pH of 2 to 3 by adding a 1N hydrochloric acid, and extracted with ethyl acetate. The ethyl acetate layer was washed with water, dried over anhydrous magnesium sulfate, and evaporated under reduced pressure to obtain 288 mg of 2-(1-naphthylmethyl)-3-morpholinocarbonylpropionyl-L-leucine as a white powder.

$Rf_1$: 0.43
IR (KBr): $\nu co$ 1720, 1620 $cm^{-1}$

Example 1

Isopropyl (2RS, 3S)-3-{N-[2-(1-naphthylmethyl)-3-(morpholinocarbonyl)propionyl]-L-alanyl}amino-2-hydroxy-5-methylhexanoate To a solution of 79 mg of 2-(1-naphthylmethyl)-3-morpholinocarbonylpropionic acid and 90 mg of isopropyl (2RS, 3S)-3-(L-alanyl)amino-2-hydroxy-5-methylhexanoate hydrochloride in 5ml of N,N-dimethylformamide were added 0.062 ml of diphenylphosphoryl azide and 0.110 ml of triethylamine under ice-cooling, and the mixture was stirred overnight. The reaction mixture was evaporated under reduced pressure, and to the residue was added a 5% aqueous sodium bicarbonate solution. The mixture was extracted with ethyl acetate. The ethyl acetate layer was washed with water, dried over anhydrous magnesium sulfate, and evaporated under reduced pressure. The residue was purified by preparative silica gel thin layer chromatography (developing solvent: chloroform/methanol = 5/1 by volume: $Rf_2$ =0.70) to obtain 19 mg of isopropyl (2RS, 3S)-3-{N-[2-(1-naphthylmethyl)-3-(morpholinocarbonyl)propionyl]-L-alanyl}amino-2-hydroxy-5-methylhexanoate as a white powder.

Melting point: 178°–183° C.
$Rf_1$: 0.77
$Rf_2$: 0.70
MS: $MH^+$, 584

Example 2

The following compounds were prepared in an analogous manner described in Example 1.

Isopropyl (2RS, 3S)-3-{N-[2-(1-naphthylmethyl)-3-(2S-methoxycarbonylpyrrolidinocarbonyl)propionyl]-L-alanyl}amino-2-hydroxy-5-methylhexanoate Melting point: 66°-69° C. (white powder)
Rf$_1$: 0.67
Rf$_2$: 0.66
MS: MH+, 626

Isopropyl (2RS, 3S)-3-{N-[2-(1-naphthylmethyl)-3-(N-methyl-N-methoxycarbonylmethylcarbamoyl)propionyl]-L-alanyl}amino-2-hydroxy-5-methylhexanoate Melting point: 65°-68° C. (white powder)
Rf$_1$: 0.75
Rf$_2$: 0.63
MS: MH+, 600

Isopropyl (2RS, 3S)-3-{N-[2-(1naphthylmethyl)-3-(morpholinocarbonyl)propionyl]-L-leucyl}amino-2-hydroxy-5-methylhexanoate Melting point: 62°-67° C. (white powder)
Rf$_1$: 0.63
Rf$_2$: 0.61
MS: MH+, 626

Isopropyl (2RS, 3S)-3-{N-[2-(1-naphthylmethyl)-3-(morpholinocarbonyl)propionyl]-L-valyl}amino-2-hydroxy-5-methylhexanoate Melting point: 55°-59° C. (white powder)
Rf$_1$: 0.68
Rf$_2$: 0.64
MS: MH+, 612

Isopropyl (2RS 3S)-3-{N-[2-(1-naphthylmethyl)-3-(morpholinocarbonyl)propionyl]-L-phenylalanyl}amino-2-hydroxy-5-methylhexanoate Melting point: 83°-86° C. (white powder)
Rf$_1$: 0.90
Rf$_2$: 0.82
MS: MH+, 660

Isopropyl (2RS 3S)-3-{N-[2-(1-naphthylmethyl)-3-(morpholinocarbonyl)propionyl]-L-tryptophyl}amino-2-hydroxy-5-methylhexanoate Melting point: 91°-94° C. (white powder)
Rf$_1$: 0.75
Rf$_2$: 0.60
MS: MH+, 699

Isopropyl (2RS, 3S)-3-{N-[2-(1naphthylmethyl-3-(morpholinocarbonyl)propionyl]-L-seryl}amino-2-hydroxy-5-methylhexanoate Melting point: 82°-86° C. (white powder)
Rf$_1$: 0.56
Rf$_2$: 0.52
MS: MH+, 600

Isopropyl (2RS, 3S)-3-{N-[2-(1-naphthylmethyl)-3-(morpholinocarbonyl)propionyl]glycyl}amino-2-hydroxy-5-methylhexanoate Melting point: 78°-83° C. (white powder)
Rf$_1$: 0.88
Rf$_2$: 0.76
MS: MH+, 570

Isopropyl (2RS 3S)-3-{N-[2-(1-naphthylmethyl)-3-(morpholinocarbonyl)propionyl]-β-alanyl}amino-2-hydroxy-5-methylhexanoate Melting point: 162°-167° C.
Rf$_1$: 0.77
Rf$_2$: 0.65
MS: MH+, 584

Example 3

Methyl (2RS, 3S)-3-{N-[2-(1-naphthylmethyl)-3-(morpholinocarbonyl)propionyl]-L-leucyl}amino-2-hydroxy-5-methylhexanoate To a solution of 83 mg of N-[2-(1-naphthylmethyl)-3-(morpholinocarbonyl)propionyl]-L-leucine and 40 mg of methyl (2RS, 3S)-3-amino-2-hydroxy-5-methylhexanoate hydrochloride in 3 ml of N,N-dimethylformamide were added 0.049 ml of diphenylphosphoryl azide and 0.058 ml of triethylamine under ice-cooling, and the mixture was stirred overnight. The reaction mixture was evaporated under reduced pressure, and to the residue was added a 5% aqueous sodium bicarbonate solution. The mixture was extracted with ethyl acetate, and the ethyl acetate layer was washed with water, dried over anhydrous magnesium sulfate, and evaporated under reduced pressure. The residue was purified by preparative silica gel thin layer chromatography (developing solvent: chloroform/methanol = 10/1 by volume: Rf = 0.43) to obtain 43 mg of methyl (2RS, 3S)-3-{N-[2-(1-naphthylmethyl)-3-(morpholinocarbonyl)propionyl]-L-leucyl}amino-2-hydroxy-5-methylhexanoate as a white powder.

Melting point: 69°-70° C.
Rf$_1$: 0.66
Rf$_2$: 0.63
MS: MH+598

Example 4

The following compound was prepared in an analogous manner described in Example 3.

N-[2-(1-Naphthylmethyl)-3-(morpholinocarbonyl)-propionyl]-L-leucyl-statiyl isoamylamide Melting point: 65°-70° C. (white powder)
Rf$_1$: 0.67
Rf$_2$: 0.65
MS: MH+667

Test Example 1

Human renin-sheep renin substrate reaction system in vitro

To a mixture containing 200 μl of a 125 mM pyrophosphate buffer (pH 7.4), 25 μl of a 20 mM aqueous solution of L-phenylalanyl-L-alanyl-L-prolin as an angiotensin converting enzyme inhibitor, 50 μl of semipurified sheep renin substrate (2000 ng angiotensin I/ml), 50 μl of dimethyl sulfoxide solution of an amino acid derivative of the present invention or 50 μl of dimethyl sulfoxide as a control and 150 μl of deionized water was added 25 μl of purified human renin (20-30 ng angiotensin I/ml/hr). The mixture was incubated for 15 minutes on a water bath at 37° C., and the reaction mixture was allowed to stand for 5 minutes on a water bath at 100° C. to stop the reaction. After cooling, 200 μl of the solution were taken out and the amount of angiotensin I produced by the addition of renin was determined by radioimmunoassay. The inhibitory effect was calculated by the following equation.

Inhibition (%) =

$$\frac{\text{Amount of angiotensin I in control} - \text{Amount of angiotensin I in a mixture containing a compound of this invention}}{\text{Amount of angiotensin I in control}} \times 100$$

The molar concentration which produced a 50% inhibition ($IC_{50}$) was calculated from the inhibition value obtained, and the results are shown below.

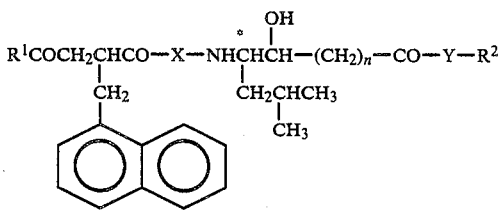

| No. | $R^1$ | X | C* | n | Y | $R^2$ | $IC_{50}$ (molar concentration) |
|---|---|---|---|---|---|---|---|
| 1 | morpholino (O N—) | Ala | S | 0 | —O— | —CH(CH$_3$)$_2$ | $2.6 \times 10^{-8}$ |
| 2 | morpholino | Leu | S | 0 | —O— | —CH(CH$_3$)$_2$ | $1.4 \times 10^{-8}$ |
| 3 | morpholino | Leu | S | 0 | —O— | —CH$_3$ | $3.0 \times 10^{-8}$ |
| 4 | morpholino | Leu | S | 1 | —NH— | —(CH$_2$)$_2$CH(CH$_3$)$_2$ | $8.0 \times 10^{-8}$ |
| 5 | morpholino | Val | S | 0 | —O— | —CH(CH$_3$)$_2$ | $6.6 \times 10^{-9}$ |
| 6 | morpholino | Phe | S | 0 | —O— | —CH(CH$_3$)$_2$ | $4.8 \times 10^{-8}$ |
| 7 | morpholino | Trp | S | 0 | —O— | —CH(CH$_3$)$_2$ | $2.9 \times 10^{-7}$ |
| 8 | morpholino | Ser | S | 0 | —O— | —CH(CH$_3$)$_2$ | $2.6 \times 10^{-8}$ |
| 9 | morpholino | Gly | S | 0 | —O— | —CH(CH$_3$)$_2$ | $3.9 \times 10^{-7}$ |

-continued

| No. | R¹ | X | C* | n | Y | R² | IC$_{50}$ (molar concentration) |
|---|---|---|---|---|---|---|---|
| 10 | morpholino (O N—) | β-Ala | S | 0 | —O— | —CH(CH$_3$)$_2$ | $1.3 \times 10^{-7}$ |
| 11 | pyrrolidinyl with COOMe (N— / COOMe) | Ala | S | 0 | —O— | —CH(CH$_3$)$_2$ | $5.9 \times 10^{-8}$ |
| 12 | Me\N—/MeOOCCH$_2$ | Ala | S | 0 | —O— | —CH(CH$_3$)$_2$ | $1.5 \times 10^{-8}$ |

Test Example 2

Renin inhibitory effect in a human high renin plasma

The mixture consisted of 500 μl of human high renin plasma, 50 μl of 20 mM L-phenylalanyl-L-alanyl-L-prolin, an angiotensin converting enzyme inhibitor, 350 μl of 0.5 M phosphate buffer (pH 7.0) containing 14 mM EDTA·2Na and 0.3% neomycin and 100 μl of appropriate concentration of amino acid compound of the present invention dissolved in DMSO or DMSO as a control. A 200 μl sample was taken out from the solution, and was cooled at 4° C. in an ice bath. The remaining sample (800 μl) was incubated for 60 minutes at 37° C. in a water bath. A 200 μl of sample was taken out from the incubated mixture, and chilled immediately in an ice bath. The amount of angiotensin I produced in both samples was determined by radioimmunoassay, and the net amount was estimated as a difference between the samples incubated at 37° C. and the sample cooled at 4° C.

The inhibitory effect was calculated by the following equation:

$$\text{Inhibitory effect (\%)} = \frac{\text{Amount of angiotensin in control} - \text{Amount of angiotensin in a mixture containing a compound of this invention}}{\text{Amount of angiotensin in control}} \times 100$$

The molar concentration which produced 50% inhibition (IC$_{50}$) was calculated from the inhibition value obtained, and the results are shown below.

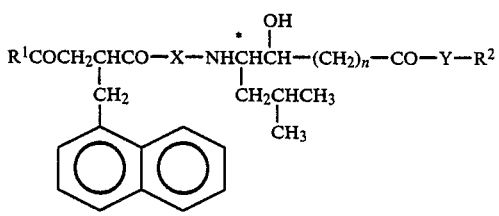

| No. | R¹ | X | C* | n | Y | R² | IC$_{50}$ (molar concentration) |
|---|---|---|---|---|---|---|---|
| 1 | morpholino | Ala | S | 0 | —O— | —CH(CH$_3$)$_2$ | $2.0 \times 10^{-8}$ |
| 2 | morpholino | Leu | S | 0 | —O— | —CH(CH$_3$)$_2$ | $1.6 \times 10^{-8}$ |
| 3 | morpholino | Leu | S | 0 | —O— | —CH$_3$ | $1.1 \times 10^{-8}$ |
| 4 | morpholino | Leu | S | 1 | —N(H)— | —(CH$_2$)$_2$CH(CH$_3$)$_2$ | $6.1 \times 10^{-8}$ |

-continued

| No. | R¹ | X | C* | n | Y | R² | IC$_{50}$ (molar concentration) |
|---|---|---|---|---|---|---|---|
| 5 | morpholino-N— | Val | S | 0 | —O— | —CH(CH$_3$)$_2$ | $3.3 \times 10^{-9}$ |
| 6 | morpholino-N— | Phe | S | 0 | —O— | —CH(CH$_3$)$_2$ | $1.4 \times 10^{-7}$ |
| 7 | morpholino-N— | Trp | S | 0 | —O— | —CH(CH$_3$)$_2$ | $5.1 \times 10^{-7}$ |
| 8 | morpholino-N— | Ser | S | 0 | —O— | —CH(CH$_3$)$_2$ | $7.2 \times 10^{-9}$ |
| 9 | morpholino-N— | Gly | S | 0 | —O— | —CH(CH$_3$)$_2$ | $2.0 \times 10^{-7}$ |
| 10 | morpholino-N— | β-Ala | S | 0 | —O— | —CH(CH$_3$)$_2$ | $4.6 \times 10^{-8}$ |
| 11 | 2-(methoxycarbonyl)pyrrolidin-1-yl (N— with COOMe) | Ala | S | 0 | —O— | —CH(CH$_3$)$_2$ | $4.4 \times 10^{-8}$ |
| 12 | Me\N—/MeOOCCH$_2$ | Ala | S | 0 | —O— | —CH(CH$_3$)$_2$ | $1.3 \times 10^{-8}$ |

Test Example 3

Hypotensive effect in marmoset

The experiment was carried out by using common marmoset as described in K. G. Hofbauer et al., *Clinical and Experimental hypertension*, Vol. A5, Nos. 7 & 8 (1983), pages 1237–1247.

Furosemide was orally administered three times to common marmoset at 15 mg per kilogram per day every other day to create a high renin state. Blood pressure of conscious marmoset was measured 3 days after the last administration of furosemide.

Measurement of blood pressure

A conscious male marmoset weighing 360 g was binded on a monkey chair, and tailarterial pressure was recorded on a pretismograph. The amino acid compound of the present invention, administred orally using a catheter. The results obtained are shown below.

(a) Compound: Isopropyl (2RS, 3S)-3-{N-[2-(1-naphthylmethyl)-3-(morpholinocarbonyl)propionyl]-L-alanyl}amino-2-hydroxy-5-methylhexanoate Dose: 30 mg/kg

| Time after administration (hours) | Blood pressure (mmHg) |
|---|---|
| Control | 84.3 |
| 1 | 75.8 |
| 2 | 70.0 |
| 3 | 70.0 |
| 5 | 70.0 |
| 7 | 72.6 |

What is claimed is:

1. An amino acid derivative represented by the formula:

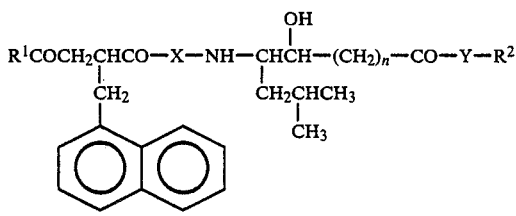

wherein R¹ represents

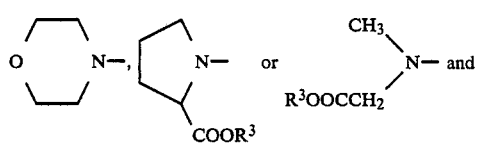

in which R³ represents a lower alkyl group, X represents an amino residual group selected from glycine, alanine, β-alanine, valine, leucine, phenylalanine, tryptophane and serine, n is zero or 1, Y represents —O—, or —NH—, and R² represents a straight- or branched-chain alkyl group having 1 to 7 carbon atoms, and a pharmaceutically acceptable salt thereof.

2. An amino acid derivative as claimed in claim 1 represented by formula:

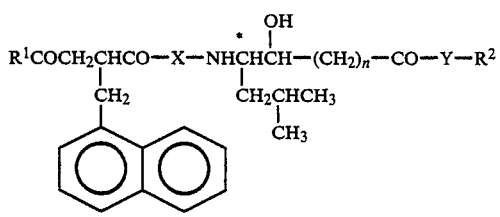

C represents a carbon atom in the S-configuration, R¹, X, n, Y and R² have the same meanings as defined above, and a pharmaceutically acceptable salt thereof.

3. An amino acid derivative as claimed in claim 2 represented by formula:

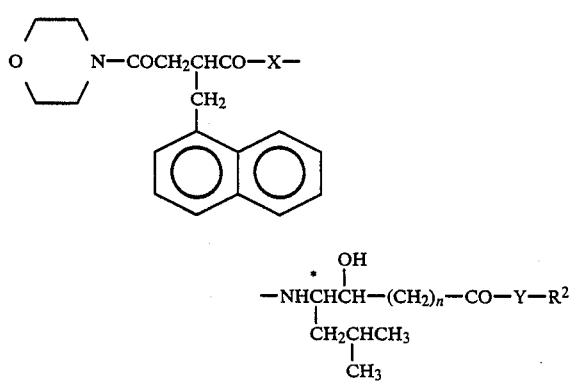

wherein X, C, n, Y and R² have the same meanings as defined above, and a pharmaceutically acceptable salt thereof.

4. The amino acid derivative as claimed in claim 3 represented by formula:

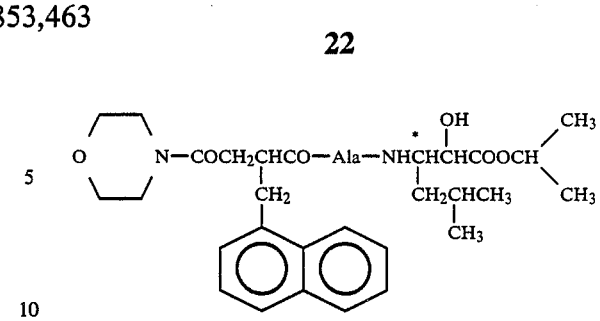

wherein Ala represents an L-alanyl group, C has the same meaning as defined above, and a pharmaceutically acceptable salt thereof.

5. The amino acid derivative as claimed in claim 3 represented by formula:

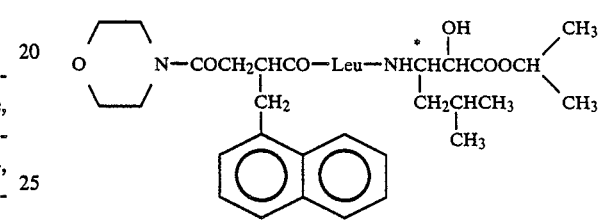

wherein Leu represents an L-leucyl group, and C has the same meaning as defined above, and a pharmaceutically acceptable salt thereof.

6. The amino acid derivative as claimed in claim 3 represented by formula:

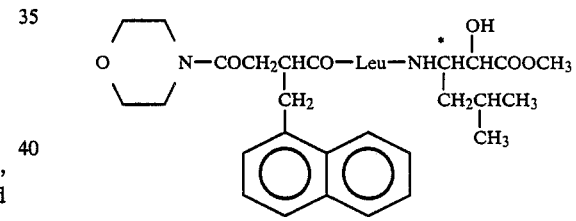

wherein Leu and C have the same meanings as defined above, and a pharmaceutically acceptable salt thereof.

7. The amino acid derivative as claimed in claim 3 represented by formula:

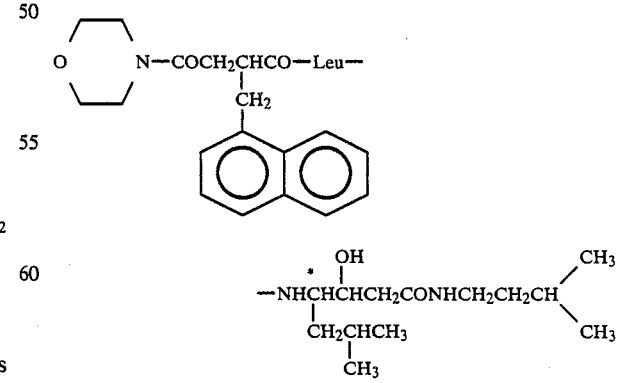

wherein Leu and C have the same meanings as defined above, and a pharmaceutically acceptable salt thereof.

8. The amino acid derivative as claimed in claim 3 represented by formula:

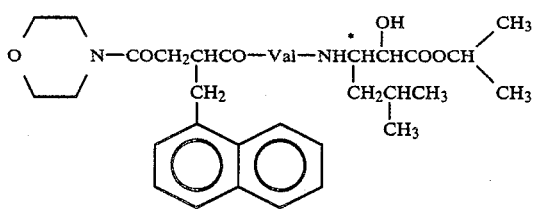

wherein Val represents a valyl group, and C has the same meaning as defined above, and a pharmaceutically acceptable salt thereof.

9. The amino acid derivative as claimed in claim 3 represented by formula:

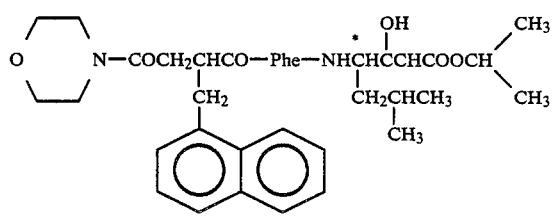

wherein Phe represents an L-phenylalanyl group, C has the same meaning as defined above, and a pharmaceutically acceptable salt thereof.

10. The amino acid derivative as claimed in claim 3 represented by formula:

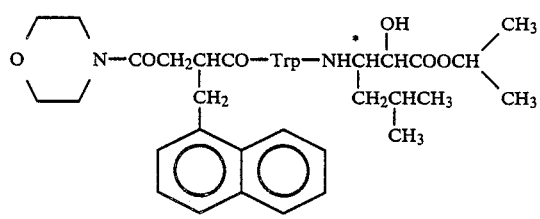

wherein Trp represents an L-tryptophyl group, C has the same meaning as defined above, and a pharmaceutically acceptable salt thereof.

11. The amino acid derivative as claimed in claim 3 represented by formula:

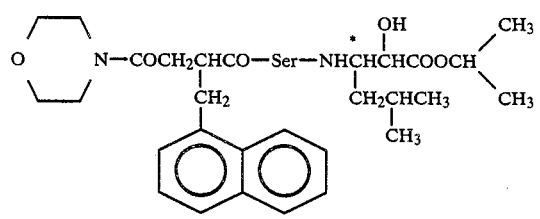

wherein Ser represents an L-seryl group, C has the same meaning as defined above, and a pharmaceutically acceptable salt thereof.

12. The amino acid derivative as claimed in claim 3 represented by formula:

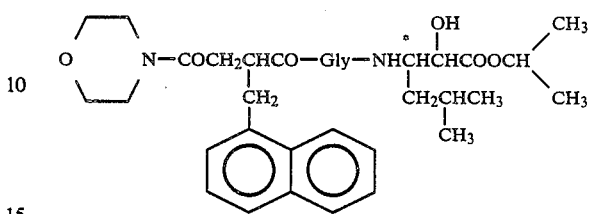

wherein Gly represents a glycyl group, C has the same meaning as defined above, and a pharmaceutically acceptable salt thereof.

13. The amino acid derivative as claimed in claim 3 represented by formula:

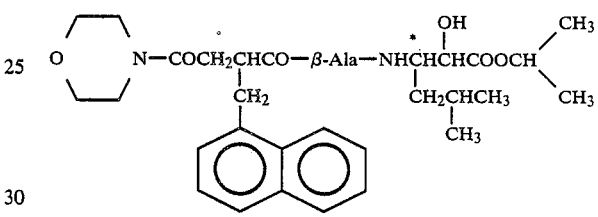

wherein $\beta$-Ala represents an $\beta$-alanyl group, C has the same meaning as defined above, and a pharmaceutically acceptable salt thereof.

14. The amino acid derivative as claimed in claim 2 represented by formula:

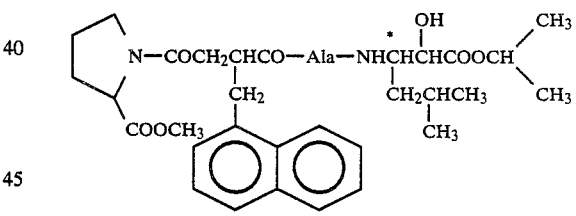

wherein Ala and C have the same meanings as defined above, and a pharmaceutically acceptable salt thereof.

15. The amino acid derivative as claimed in claim 2 represented by formula:

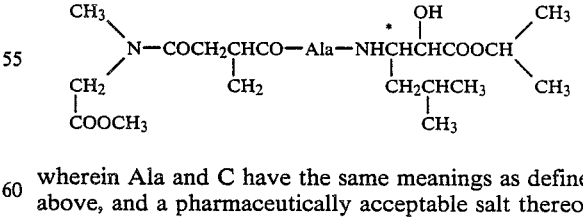

wherein Ala and C have the same meanings as defined above, and a pharmaceutically acceptable salt thereof.

* * * * *